(12) United States Patent
Marincak (10) Patent No.: US 8,059,008 B2
(45) Date of Patent: Nov. 15, 2011

(54) SURFACE-MOUNTED CRACK DETECTION (75) Inventor: Anton Marincak, Stittsville (CA)

(73) Assignee: National Research Council of Canada, Ottawa, ON (*) Notice: Subject to any disclaimer, the term of this patent is extended or adjusted under 35 U.S.C. 154(b) by 507 days.

(21) Appl. No.: 12/223,072

(22) PCT Filed: Sep. 20, 2006

(86) PCT No.: PCT/CA2006/001549
§ 371 (c)(1),
(2), (4) Date: Jul. 22, 2008

(87) PCT Pub. No.: WO2007/085070
PCT Pub. Date: Aug. 2, 2007

(65) Prior Publication Data
US 2010/0225497 A1  Sep. 9, 2010

Related U.S. Application Data (60) Provisional application No. 60/762,158, filed on Jan. 26, 2006.

(51) Int. Cl.
*G08B 21/00* (2006.01)
(52) U.S. Cl. ........ 340/657; 340/660; 340/664; 324/691; 324/713; 73/779; 73/776
(58) Field of Classification Search .................. 340/657, 340/660, 664; 324/233, 633, 220, 718, 238, 324/242, 232, 44, 691, 713; 73/799, 776, 73/773
See application file for complete search history.

(56) References Cited

U.S. PATENT DOCUMENTS

| 3,803,485 | A | * | 4/1974 | Crites et al. | 324/693 |
|---|---|---|---|---|---|
| 4,107,672 | A |   | 8/1978 | Van Riemsdijk et al. | |
| 4,255,974 | A | * | 3/1981 | Dufrane et al. | 73/776 |
| 4,484,132 | A | * | 11/1984 | Crites | 324/557 |
| 4,674,235 | A |   | 6/1987 | Inoue | |
| 6,126,758 | A | * | 10/2000 | Meelu et al. | 148/258 |
| 2005/0223812 | A1 | * | 10/2005 | Denis | 73/799 |
| 2005/0284232 | A1 | * | 12/2005 | Rice | 73/762 |
| 2006/0082366 | A1 | * | 4/2006 | Goldfine et al. | 324/240 |

FOREIGN PATENT DOCUMENTS

| JP | 05340912 | * 12/1993 | .................. 324/658 |
| WO | WO 2005-003486 | 1/2005 | |

OTHER PUBLICATIONS

International Preliminary Report on Patentability for PCT/CA2006/001549 dated Jul. 29, 2008.
International Search report for PCT/CA2006/001549 dated Dec. 28, 2006.
Hiroo et al. Abstract of JP 02034587 published Feb. 5, 1990.
Masataka et al. Abstract of JP 01281181 published Nov. 13, 1989.
Michio et al. Abstract of JP 04114619 published Apr. 15, 1992.
Kiyokimi et al. Abstract of JP 59042443 published Mar. 9, 1984.
Tamio et al. Abstract of JP 4115151 published Apr. 16, 1992.

* cited by examiner

*Primary Examiner* — Jennifer Mehmood
*Assistant Examiner* — Hongmin Fan
(74) *Attorney, Agent, or Firm* — Jason E. J. Davis (57) ABSTRACT

A cementitious compound provides a brittle undercoat for making a surface-mounted crack sensor on a surface. A low percent elongation and low tensile strength of the cementitious compound have proven valuable in ensuring that cracks in the underlying surface are transmitted through the undercoat so that a trace of conductive ink or paint on the undercoat more reliably detects the crack.

23 Claims, 4 Drawing Sheets

SURFACE-MOUNTED CRACK DETECTION

CROSS-REFERENCE TO RELATED APPLICATIONS

This application is a national entry of International Application PCT/CA2006/001549 filed Sep. 20, 2006, and claims the benefit of U.S. Provisional application Ser. No. 60/762,158 filed Jan. 26, 2006.

BACKGROUND OF THE INVENTION

This invention relates in general to the field of non-destructive testing, and in particular to the detection of cracks on a surface using a surface-mounted sensor.

In many mechanical and civil devices, structures are used for mechanical supports that are susceptible to cracking. Frequently due to loading conditions and stress concentrations, certain parts of structural surfaces are known to have a higher risk of cracking than others. Cracks caused or assisted by fluctuating loading, degradation of a composition, etc. are significant problems in a wide variety of areas. The testing of materials, bonds between materials, and components under environmental and stress conditions is often used to determine safe operating regimes for many critical structures, according to their composition, shape, etc. Fatigue testing of materials is used, for example, in the aeronautics industry. Both in this testing, and as in deployed structures, it is useful to provide low cost, reliable, crack sensing.

Conventional coupon fatigue tests require constant supervision and visual monitoring of crack formation/growth, for example, to stop the test once a crack has formed and grown to a desired length. Such tests are therefore labour intensive, and time consuming, and can only be run during working hours.

One prior art approach to the problem uses commercially available crack detection gauges, which incorporate a wire grid electrical conductor applied to a flexible substrate that are bonded onto the surface of a test specimen. Unfortunately, such apparatus does not work effectively. Cracks tend to form and pass under the commercially available crack detection gauges or reconnect once the crack closes after the load is removed and thus do not reliably break the electrical circuit used to sense the crack.

In another approach, Japanese published application no. 02236508, (publication no. 4115151) of Oi Tamio et al. (1992) teaches the detection of fine cracks in a test object, using a brittle, electrically insulating tape bonded to the test object. A problem with this approach is that the tape has to be physically applied to the surface, which due to its brittle nature, is susceptible to cracking on installation. It may be impossible or exceedingly difficult to apply such a tape to uneven test surfaces. Moreover, in our experience, stick on layers have bonding problems, and if a circuit peels, it cannot sense a crack underneath it. Furthermore the electrical test circuit, which is expected to break when a crack forms in some situations may reconnect when the crack closes, failing to raise alarms in some cases, or requiring more expensive sampling equipment for reliable detection, if reliable detection is possible. Such sampling equipment may be larger, and may require a power supply. It may be difficult to continue sampling the system while it is in use because of obstructions, etc.

SUMMARY OF THE INVENTION

According to the teachings of this invention, a surface-mounted, customizable crack sensor may be obtained.

One aspect of the invention is the use of a cementitious compound to form a brittle undercoat between a surface, and a trace of an electrically conductive ink or paint, to define a surface-mounted crack sensor for sensing a crack in the surface that crosses the trace.

The cementitious compound is preferably formed with a particle and a binder so that it crumbles when broken. For example, the cementitious compound may consist of a cement having a base of alumina, magnesia, silica, or zirconia ceramics. The cementitious compound may consist of a thermocouple cement.

Another aspect of the invention is an apparatus useful for detecting a crack on a region of a surface. The apparatus comprises an electrically insulating undercoat on the surface, said undercoat comprising a cementitious compound, and a trace of an electrically conductive ink or paint on the undercoat between at least two terminals for connection to a voltage detector. The trace defines at least one region that permits an interrogator to determine a continuity of the trace.

The trace may consist of a plurality of traces arrayed to provide indications of a size of a crack, or to identify a position of the crack.

In accordance with yet another aspect of the invention, an article having the surface and the apparatus is provided.

The article may further comprise a voltage detector with current probes secured to terminals of the trace. The voltage detector may have electronics for outputting an indicator of an outcome of a voltage determination. The indicator may be provided to one of a computer, and a controller, to provide notification of a condition of the surface. The electronics may provide a wireless communications function, such as a radio frequency identification tag. The electronics may be mounted to the surface.

In accordance with a further aspect of the invention, a method for monitoring a surface for deformation is provided is provided. The method involves applying a cementitious compound to the surface to form a brittle undercoat, applying an electrically conductive trace on the undercoat, and assessing electrical conductivity of the trace.

In accordance with further aspects of the invention, kits for producing surface-mounted crack sensors are provided. The kits include at least one of the cementitious compound and instructions for applying a cementitious compound to form a brittle undercoat and applying an electrically conductive ink or paint on the undercoat to define a trace, and at least one other component of an embodiment of the invention. The kits may also include the electrically conductive ink or paint; an RFID tag; a pattern-form device for producing the trace; or a thin film conductive surface.

Further advantages and a better understanding of the invention and its objects is possible having regard to the detailed description of the invention with the attached drawings.

DETAILED DESCRIPTION OF THE INVENTION

The present invention provides a surface-mounted, customizable crack detection technique. Herein 'crack' is used to mean any kind of surface displacement phenomenon whereby one part of the surface moves relative to another by a significant amount. The term includes cracks or fissures that open and close under cyclic loading (or other time-dependent phenomena). Accordingly the crack detection technique may be used when the surface cleaves in such a way as to rejoin in an apparently seamless manner when a stress is removed, for example. The term also includes cracks caused by shearing movement, crumpling, bulging, and folding where a minimum radius of curvature is less than a threshold, and even plastic deformations of the surface (of a minimum distance), where no breach of the surface is yet pronounced.

Figure 1:
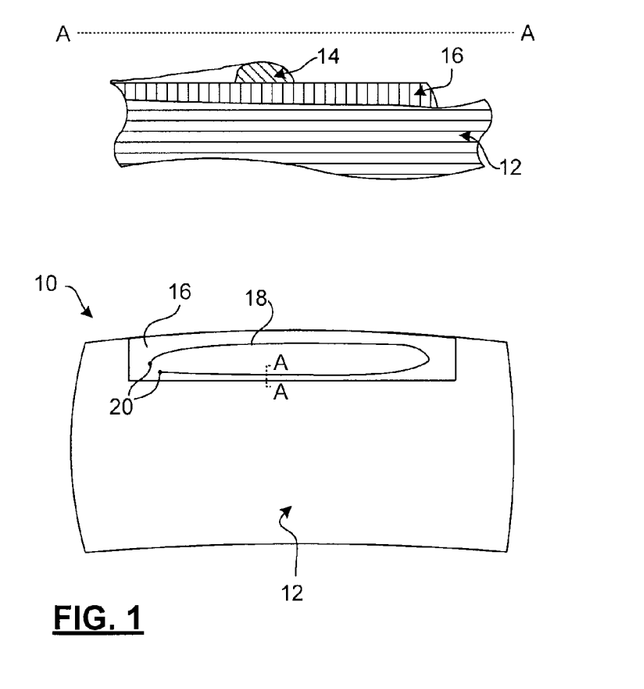
FIG. 1 is a schematic illustration of a surface-mounted crack sensor in accordance with an embodiment of the invention.

FIG. 1 schematically illustrates a surface-mounted crack sensor 10 applied on a structural surface 12. In some embodiments the invention may be applied to materials testing, in which case the structural surface 12 may be a side of a coupon of a material having a defined property, or a surface of a test piece or model that is subjected to a test. Alternatively, the surface 12 may be on a critical structural surface of a structure in use. For example, the surface 12 may be on a critical component of an aerospace structure, a motorized vehicle, a building, bridge, or tunnel, or on a pipe. The structural surface 12 may be on a skin covering other components. The structural surface 12 may have a wide variety of surface geometries.

The surface-mounted crack sensor 10 includes an electrically conductive paint or ink 14 applied on top of an undercoat 16 that acts as an electrical insulator. The undercoat 16 is applied to the structural surface 12. The electrically conductive paint or ink 14 is applied on the undercoat 16 to define at least one trace 18 between a pair of terminals 20. The trace 18 passes across a region on the surface 12 susceptible to cracking. The trace 18 of electrically conductive paint or ink 14 and the undercoat 16 fracture together, if the structural surface 12 develops a crack that passes beneath the trace 18.

The undercoat 16 is composed of a cementitious compound, and accordingly is brittle, i.e. it is susceptible to brittle fracture as opposed to ductile fracture, and accordingly has a low percent elongation, very little plastic or elastic deformation before fracturing, and the fracturing tends to absorb little energy. The percent elongation of the cementitious compound is less than 0.003 percent, preferably less than 0.001 percent, and most preferably less than 0.0006 percent. The cementitious compound also has a low tensile strength, less than 8,000 psi. Preferably the tensile strength is less than 5,000 psi, more preferably still, it is less than 2,000 psi. Most preferably the tensile strength of the cementitious compound is from 1 to 1500 psi, and still has an aggressive bond to the structural surface 12. It will be appreciated that the above-identified ranges are useful on surfaces of considerable strength, and flexibility; with conductive inks and paints that have some elasticity and strength; and for traces that are centimeters wide. In different scales, with different materials, and different applications, it will be appreciated that cementitious compounds outside of these ranges may be desirable.

The undercoat 16 provides adequate bonding for a commercially available conductive paint or ink, and an intended structural surface, and further provides electrical insulation between the conductive ink or paint, and the structural surface, which, in some applications, is conductive.

The undercoat 16 preferably has a fine particulate composition with a binding agent so that the undercoat 16 readily crumbles with minimal shear movement, but aggressively bonds to a wide variety of surfaces. Applicant has found that certain ceramic-based materials having fine crystalline components with a binder to provide an exemplary undercoat, although other particulate compositions may also work. Cementitious compounds provide adequate bonding of commercially available conductive paints and inks and a wide variety of surfaces, and further provide electrical insulation. High temperature ceramic-based compounds, such as those used for potting, casting or otherwise covering thermocouples (herein called thermocouple cements), have been found to have all of the desired properties for providing an insulating undercoat. Commercially available thermocouple cements have alumina, magnesia, silica, and zirconia ceramic bases.

While not being limited by the following theory, it is believed that the applicability of the cementitious compounds to surfaces in use under time-varying loading, is in part due to their aggressive bonding to the surface 12. The surface 12 will normally flex and exhibit nominal, incidental, surface deformations, resulting in cracking of the undercoat 16. These cracks will naturally extend through the undercoat 16 substantially normal to the surface 12. But for any reasonable thickness of the cementitious compounds (generally a thin film is desired) a strength of a bond to the surface 12 will prevent spalling and chipping, and so maintain integrity of a substantial part of the undercoat 16. This integrity is sufficient for maintaining required support for the trace 18, which is substantially more elastic and will not break if a thin crack in the undercoat 16 is produced. The break in the trace 18, is at least in part due to crumbling and effacement of the undercoat 16, which causes a persistent gap considerably wider that the thin crack caused by normal flexure of the surface 12. The crumbling and effacement favours that even if the crack in the underlying structural surface 12 is closed at a time of measurement, the trace 18 will remain broken. This alleviates problems of failed detection in some application environments, especially if interrogation of the surface-mounted crack sensor 10 is most easily performed when the surface 12 is not under a time-varying load.

The undercoat 16 may be painted on, or applied in a number of ways known in the art, for example using electrostatic deposition. For example it may be painted on by brush, roll, or spray. It may be applied through a template, for example made of silk screen-type material. The precise thickness of the undercoat 16 need not be controlled for most applications because excess thickness does not appreciably vary the brittleness of the undercoat 16 on one hand, and because the undercoat 16 need only be thick enough to provide electrical insulation as required by the application, on the other. In many embodiments thinness is preferred to reduce a bulk added by the surface-mounted crack sensor 10. Most cementitious compounds cease to have the desired anti-spalling properties if applied in too great a thickness, and cease to have a desired electrical insulation if applied in too thin a coat, but most application methods will not produce a coat that approaches either of these limits.

In some applications the structural surface 12 is conductive, and the undercoat 16 must be of a thickness and composition to provide adequate electrical insulation between the structural surface 12 and the conductive ink or paint 14, to permit the detection of the test voltage applied across the trace 18 with a desired reliability. If the structural surface 12 is not conductive, the undercoat 16 need only be enough of an insulator so that conduction through the undercoat 16 does not interfere with the measurement of the test voltage resulting in an undesired reliability.

The conductive ink or paint 14 may be applied over the undercoat 16 using any number of application techniques known in the art. These include: using pens that allow for manual drawing of the trace 18; application (for example, by roller, brush or spray) through a silk-screen or other template; using a stamp, for example, of rubber; application by an ink jet; and using a pad printer (with a roller or block). Using a pad printer, stamp or application through a template, a pattern-form on a block, roller, template, or stamp is used to define the trace. It will be appreciated that depending on the surface to be used, shape of the pattern of the trace, accessibility constraints, surface properties, etc., different methods of application may be preferred, and different surface preparation steps may be required.

The following are examples of commercially available conductive inks or paints: acrylic resin containing metallic silver (e.g. Permatex® Quick Grid™); copper particle conductivity in a water based paint (e.g. CuPro-Cote™ paint); silver filled, acrylic based paint; silver particle conductive epoxies; carbon filled, polyimide based paint; carbon filled, epoxy based paint; nickel-filled epoxy based paint; silver powder in a methyl methacrylate binder ink; super shield liquid format (also called nickel print): and acrylic base high purity nickel flake paint.

The terminals 20 of the trace 18 can be formed of a tab, a recess or other feature that permits coupling to a probe of an electronic interrogator. The feature may be composed of another material that is secured to the surface 12 and/or undercoat 16, and makes reliable electrical connection with the trace 18. In some embodiments the feature may be an area of the trace 18 having a greater diameter.

Figure 2:
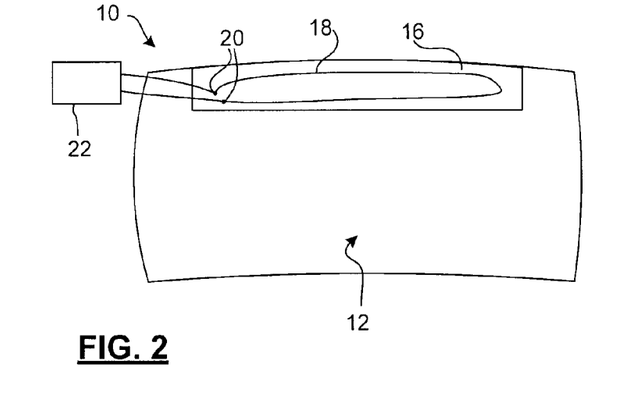
FIG. 2 is a schematic illustration of the surface-mounted crack sensor shown in FIG. 1 coupled to a voltage detector in accordance with an embodiment of the invention.

FIG. 2 is a schematic illustration of the surface-mounted crack sensor 10 coupled to an exemplary embodiment of an electronic interrogator for verifying continuity of the trace 18; a voltage detector 22. The voltage detector 22 may be a standard digital multimeter, for example, and may have an interface for communicating a measurement outcome. This communication may be provided by a visual display for a user in certain situations, but in some applications it is preferable that the output be provided to an automated system, for example to a computer or a controller for controlling automated equipment. The controller (such as an MTS Load Frame controller) may control equipment used to test crack formation on the surface 12. The computer or controller may be adapted to initiate failover procedures and/or to issue system alarms in a system in use that incorporates or relies on the structural surface, for example.

The voltage detector 22 may be a multiport I/O card that can be connected to multiple pairs of terminals, which is particularly useful if multiple terminals 20 are provided by the trace 18, or by multiple traces are provided. Examples of patterns for applying the conductive ink or paint 14 to define multiple terminals 20 are provided in FIG. 4.

In operation, probes of the voltage detector 22 are coupled to the terminals 20 of the surface-mounted crack sensor 10, resulting in a determination of whether voltage is conducted there through. If the surface 12 is cracked beneath the trace 18, conduction through the trace 18 will be broken, and substantially no voltage will be transmitted. Otherwise the trace 18 conducts voltage that is detected by the voltage detector 22, indicating that the surface 12 is not cracked beneath the trace 18.

The voltage detector 22 may be a dedicated part of a materials/component testing apparatus, in which case it may be connected to an equipment controller to halt or vary the testing of the material/component in response to crack formation, for example. The voltage detector 22 may be connected to the surface-mounted crack sensor 10 at a predetermined interval to test the surface 12. The surface-mounted crack sensor 10 can advantageously be used when visual inspection is difficult or undesirable.

Figure 3:
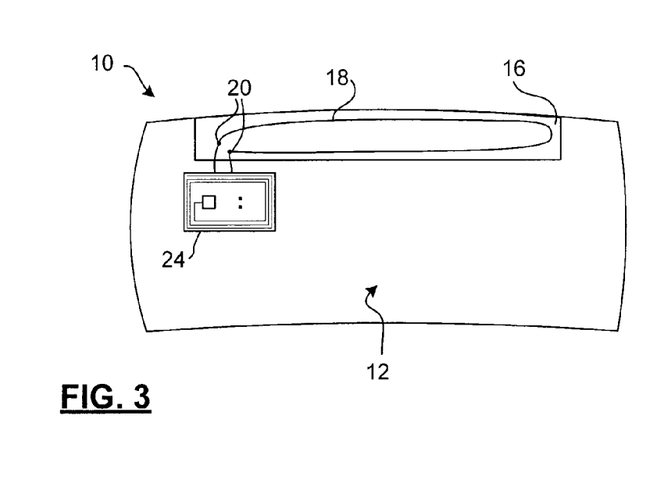
FIG. 3 is a schematic illustration of a surface-mounted crack detector featuring communications and processing electronics in accordance with an embodiment of the invention.

FIG. 3 is a schematic illustration of an embodiment of a surface-mounted crack detection apparatus that includes surface-mounted communications and processing electronics 24. Advantageously the communications and processing electronics 24 may be of a kind that is powered externally, via communications circuitry, so that there is no power supply contained in the communications and processing electronics 24. This largely facilitates embedding of the communications and processing electronics 24 on the structural surface 12, as the communications and processing electronics 24 can be paper thin, and of negligible mass (for many applications). The communications and processing electronics 24 and surface-mounted crack sensor 10 provide an integrated, closed detector that can be painted over or rendered inaccessible in use, but remains available for remote interrogation. One commercially available example of a communications and processing device 24 powered by communications circuitry is a radio frequency identification (RFID) tag. RFID tags are available that have memory and are capable of, for example, interrogating a thermometer, and logging the measurements. Such a RFID tag could be adapted for use in voltage detection.

RFID tags generally are composed of a plastic film onto which a micro chip and an antenna are attached. The antenna may be a spiral loop-type antenna known in the art.

A preferred connection between the terminals 20 and inputs of the communications and processing device 24 uses an electrically conductive epoxy because of its rigid connection, elasticity, and ease of application.

In the preceeding examples, continuity of the trace 18 was determined by connecting two terminals 20 to a voltage detector 22. A principal advantage of using voltage detection is a low power requirement: by providing a high impedance resistor in series with the surface-mounted crack sensor 10, a low power continuity test of the circuit is provided. However, it will be appreciated by those of skill in the art that other electronic interrogators could equally be used to detect a crack through the surface-mounted crack sensor 10 of FIG. 1. For example, a current through the trace 18, could be used. The current could be detected directly, or by a voltage of a constant current device well known in the art, for example. One advantage of current detection is that the current will vary with a minimum cross-section of the trace 18. The minimum cross-section being defined once the surface-mounted crack sensor 10 is constructed, any decrease in the current (or any increase in the voltage required to maintain a fixed current) corresponds to a narrowing of the minimum cross-section. Accordingly, when current detection is used, it is possible to determine a dimension of a crack running across part of the trace 18.

Figure 4:
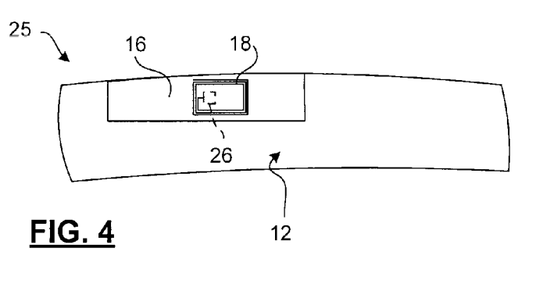
FIG. 4 is a schematic illustration of an alternative embodiment of a surface-mounted crack detector featuring communications and processing electronics with an antenna formed of an electrically conductive ink, in accordance with an embodiment of the invention.

FIG. 4 schematically illustrates an alternative embodiment of a surface-mounted crack detector 25 that uses a micro chip 26 and creates an antenna with the trace 18. In this embodiment, as before, a crack in the structural surface 12 will sever the trace 18, but the manner in which this is detected, according to the present invention, is via attempted energization of the micro chip 26 through the antenna. The micro chip 26 is energized by the efficient absorption of electromagnetic energy of a predetermined frequency (band) to which the antenna is tuned. If the antenna is broken, the energy at the predetermined frequency (band) will not be efficiently absorbed. As a result the micro chip 26 will not be energized, and further, modulation of a side band of the electromagnetic energy re-emitted by the antenna for communication will also be significantly impeded by the break in the antenna. As a result, a failure of the micro chip 26 to respond indicates a crack.

It should further be noted that in some applications of the invention, the micro chip 26 can be omitted. In these embodiments an eddy current probe can be used to excite the antenna (trace 18), and a detected response would indicate whether the electromagnetic energy at the predetermined frequency (band) had been absorbed. If the electromagnetic energy was not absorbed, it would be attributed to a break in the trace 18.

Figure 5:
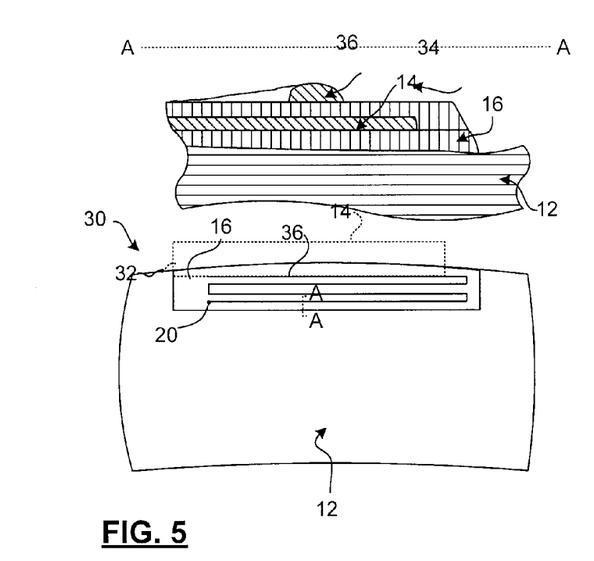
FIG. 5 is a schematic illustration of a multi-layer surface-mounted crack sensor adapted for capacitive detection in accordance with an embodiment of the invention.
Figure 6:
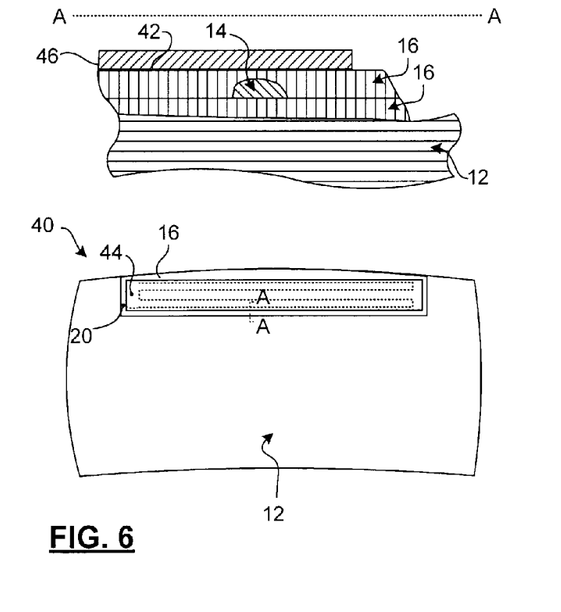
FIG. 6 is a schematic illustration of a multi-layer surface-mounted crack sensor adapted for capacitive detection using a conductive tape, in accordance with an embodiment of the invention.
Figure 7:
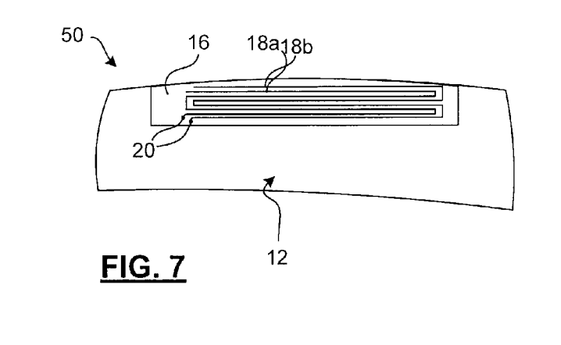
FIG. 7 is a schematic illustration of a single-layer surface-mounted crack sensor adapted for capacitive detection in accordance with an embodiment of the invention.

FIGS. 5-7 schematically illustrate embodiments of surface-mounted crack sensors that are interrogated by determining a capacitance produced between the trace 18 and a charged surface or another trace 18. As is well known in the art, when different charges build up on parallel plates that are separated by an insulator, a capacitance is produced. The capacitance varies directly with the surface area between the intersection of the surface areas of the two charged parts, inversely with a distance separating the charged parts, and depends on a dielectric constant of a medium separating the charged parts. A capacitance may be detected using a number of capacitance detection circuits that typically involve oscillators and resistors, and these capacitance detection circuits are typically tuned to a frequency that is useful for detecting the capacitance.

It will further be appreciated that if the structural surface 12 is conductive, and the undercoat 16 is a thin layer of an insulator, the surface 12 and surface-mounted crack sensor 10 define a capacitor, and this capacitance can be used to determine whether the trace 18 is broken. If the trace 18 is broken by an underlying crack, a signal applied between either terminal 20 of the trace 18 and the surface 12 will detect a smaller capacitance as a result of the smaller surface area of the capacitor. In embodiments where effacement of the undercoat 16 effectively replaces the undercoat with either a vacuum or air, this effacement only contributes to a drop in the capacitance of the capacitor, because the dielectric constant of air and vacuum are higher than that of most solids, including the cementitious compound. In some embodiments the effacement may produce a detectable drop in capacitance even before the trace 18 is entirely broken, especially if the trace 18 is particularly fat, and there are many points of effacement. In these embodiments, if different capacitance values are observed depending on which terminal 20 is supplied the voltage, or such a capacitance value is different than a reference value, a break in the trace 18 is detected. Circuitry for determining a capacitance is well known in the art, and typically includes a tuned oscillator circuit.

FIG. 5 schematically illustrates an embodiment of a surface-mounted crack sensor 30 that consists of two brittle layers. In ghost view, a rectangular trace 18 is painted across the undercoat 14, as described above. A terminal 32 is provided for electrical connection with the rectangular trace 18. The rectangular trace 18 is overlaid by a second coat 34 of cementitious compound, which may be a same cementitious compound applied to produce the undercoat 14. The second coat 34 provides a surface for receiving a parallel trace 36. The parallel trace 36 provides a terminal 20 for connection to a capacitance detector.

It will be appreciated by those of skill in the art that in alternative embodiments a same stamp can be used to form both the trace 18 and the parallel trace 36, which may be preferably superimposed to maximize the capacitance.

An advantage of the pattern of the parallel trace 36 is that the capacitance detected will decrease in steps each time the crack (originating at the edge) traverses a respective segment of the parallel trace 36, allowing a graded assessment of the integrity of the structural surface 12.

It will be noted that the rectangular trace 18 and parallel trace 36 could be switched as the cracks will pass through the multiple layers of the cementitious compound together.

FIG. 6 schematically illustrates an alternative layer for a capacitance-interrogated surface-mounted crack sensor 40. The capacitance is produced between the trace 18 (visible in ghost view) and a conductive surface 42 that is applied over the trace 18. The trace 18 is connected to terminal 20, and the conductive surface 42 is connected to a terminal 44. The surface-mounted crack sensor 40 shown has a second coat 34 to provide the insulation between the trace 18 and the conductive surface 42.

While any conductive surface 42 may be used, applicant contemplates the use of a coated film or tape 46, such as Physical Vapour Deposition (PVD) tape, to provide the conductive surface 42. PVD tape has a metallized coating on a body of an insulating plastic. As the tape 46 may have significant tensile strength and elasticity, in which case it would not be expected to fracture with the underlying crack. Whether or not the tape breaks, the surface area of the capacitor depends on the a surface area of intersection of the two charged plates (projected into a common plane), and accordingly, a brake in the trace 18 will reduce the capacitance.

It will be appreciated by those of skill in the art that the second coat 34 could be replaced by other insulating layers, such as the body 46 of a tape which provides the conductive surface 42 on a top side, rather than a bottom side as shown. One advantage of this would be an even separation of the trace 18 and the conductive surface 42. However, it will be necessary to prevent bonding of the trace 18 to the tape, which could otherwise adhere to the tape and not break with the undercoat 16.

FIG. 7 schematically illustrates a single-layer capacitance-interrogated surface-mounted crack sensor 50. Surface-mounted crack sensor 50 is composed of the same cementitious compound undercoat 16 as in previous embodiments, however there are two traces 18a and 18b which remain in parallel configuration. Effectively the capacitance produced between traces 18a,b is a property of the length of the parallel segments that are charged. If successive segments of trace 18a or trace 18b are broken, the capacitance measured between corresponding terminals 20 will drop.

The foregoing embodiments of surface-mounted crack sensors are not intended to be exhaustive, the range of specific crack sensors provided show how the cementitious compound can be used with conductive ink or paint to produce surface-mounted crack sensors.

Figure 8:
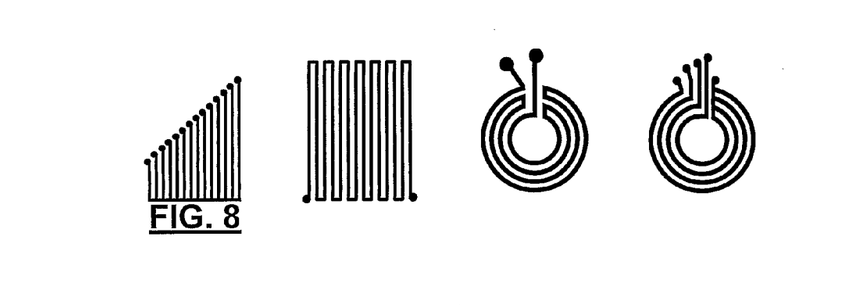
FIG. 8 is a schematic illustration of a set of templates used for applying conductive ink or paint.

FIG. 8 is a schematic illustration of a set of templates that could be used to apply one or more traces 18. Two of the templates provide for application in a place where cracks are expected in a given direction. For example, cracks are frequently expected to develop along edges of surfaces, and work their way into the surface in a direction orthogonal to the edge. In such a case, traces will logically be arranged to extend parallel to the edge. Here parallel traces can be used to determine a dimension of the crack. For example, knowing which traces have ruptured, and which have not may provide bounds for a size of the crack. This can be useful in testing to ensure that a crack in a test piece has grown to a predetermined size before automatically ending the test, or to enforce a safe operating regime that tolerates a certain number of cracks of certain dimensions. Alternatively multiple traces can be used to determine a position of the crack.

A sensitivity of the surface-mounted crack sensor can be defined by a thickness of the trace. The crack may only be detected if it spans the thickness of the trace, and so the surface-mounted crack sensor can be made of a desired sensitivity as well as of a desired spatial arrangement.

If cracks are expected to form radially from a point, for example, surrounding a single point attachment (such as a rivet), azimuthally extended traces can be provided. As before a sequence of azimuthally extended traces to provide an indicator of a size of the crack.

Figure 9A:
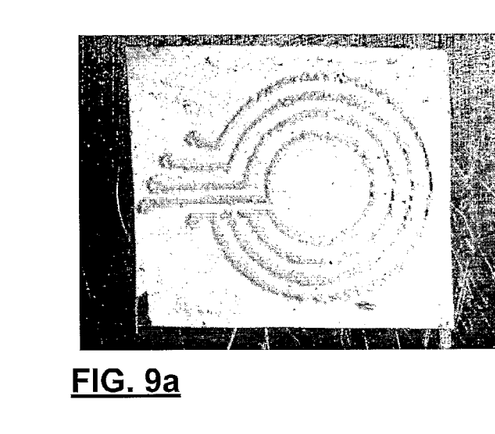
FIG. 9a is an image of an example of a surface-mounted crack sensor produced using a template shown in FIG. 8 defining multiple traces.

FIG. 9a is an image of a surface-mounted crack sensor defined using a template of FIG. 8. The surface-mounted crack sensor has four traces encircling a region, defined by five terminals. The trace is composed of MG Chemicals Silver Print™, and the undercoat is composed of Omega CC™ high temperature ceramic-based cement.

Figure 9B:
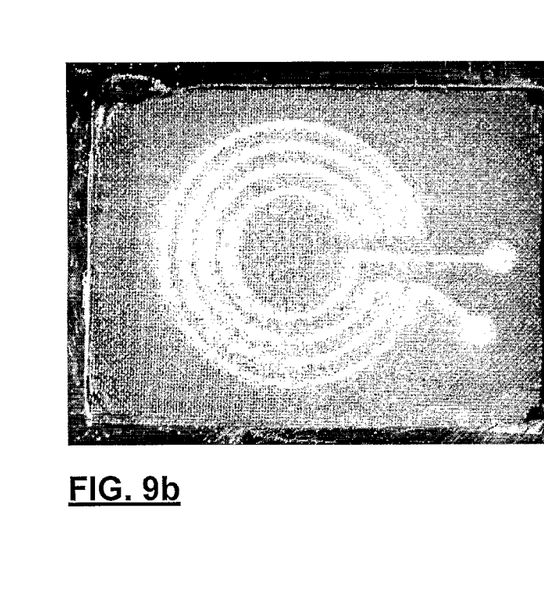
FIG. 9b is an image of a silk screen template for applying a conductive ink or paint using a template shown in FIG. 8.
Figure 9C:
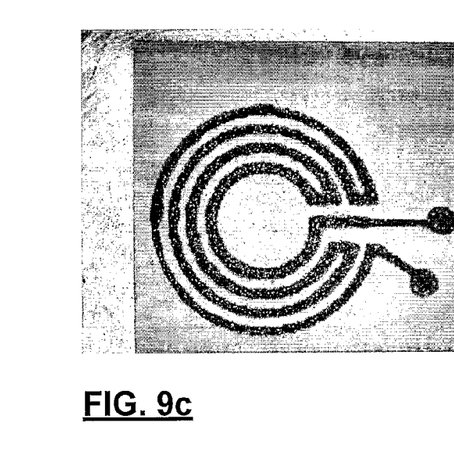
FIG. 9c is an image of an example of a surface-mounted crack sensor produced using the silk screen template shown in FIG. 9b.

FIG. 9b is an image of a silk screen template of a second shape shown in FIG. 8, prior to application of MG Chemicals Nickel Print™ The silk screen template defines one trace encircling a region between two terminals, by masking a remainder of an undercoat of Omega CC™ high temperature ceramic-based cement. FIG. 9c is an image of a surface-mounted crack sensor produced after application of the MG Chemicals Nickel Print™.

The undercoats of the surface-mounted crack sensors were tested prior to application of the conductive ink or paint to ensure adequate electrical insulation is provided throughout the surface where the traces were to be deposed.

EXAMPLE

Figure 10:
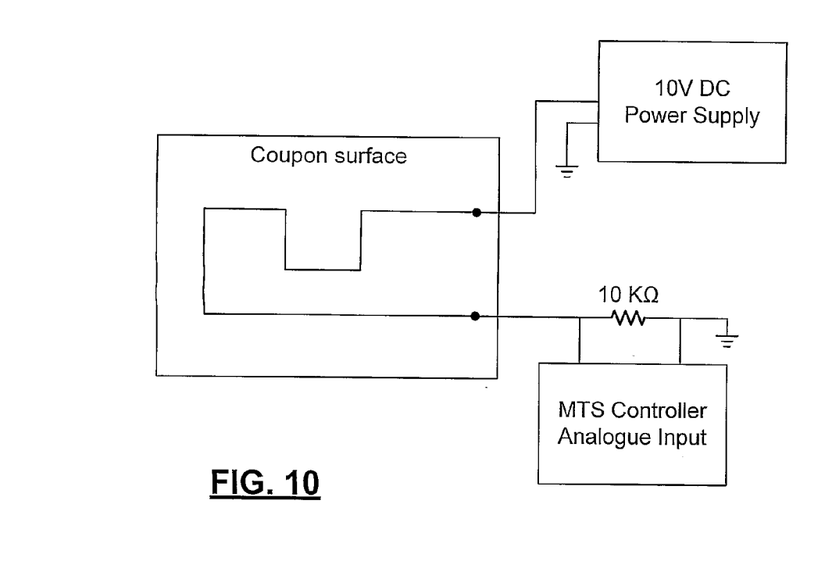
FIG. 10 is a circuit diagram of examples of an automated coupon fatigue test apparatus using a surface-mounted crack sensor.

The circuit diagram shown in FIG. 10 was used to verify the principle of the invention. The sensing circuit used a 10-volt DC power supply, which was connected to an analogue input of a computerized MTS load frame controller. The MTS load frame controller can be set to "alarm" (notify the operator by displaying a warning message) or autonomously "halt" a command program sequence immediately upon detecting a pre-set change in the signal on the analogue input circuit. When the voltage on the analog input dropped below 9 volts, the MTS load frame controller halted the test and stopped the cyclic loading. A lap joint shown in FIG. 11 stopped after 280,000 cycles.

Figure 11:
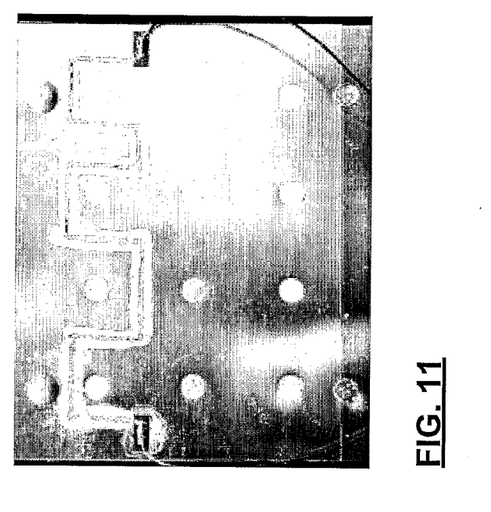
FIG. 11 is an image of a surface-mounted crack sensor applied to a riveted aluminium test coupon.

FIG. 11 is an image of a riveted, lap jointed, aluminum test coupon upon which a surface-mounted crack detection apparatus has been affixed. The undercoat was a manually painted on layer of Omega CC™ high temperature ceramic-based cement. The undercoat was found to be about 5/1000ths of an inch thick. The electrically conductive paint used was Permatex® Quick Grid™, an acrylic resin containing metallic silver, which was also painted on manually.

Figure 12:
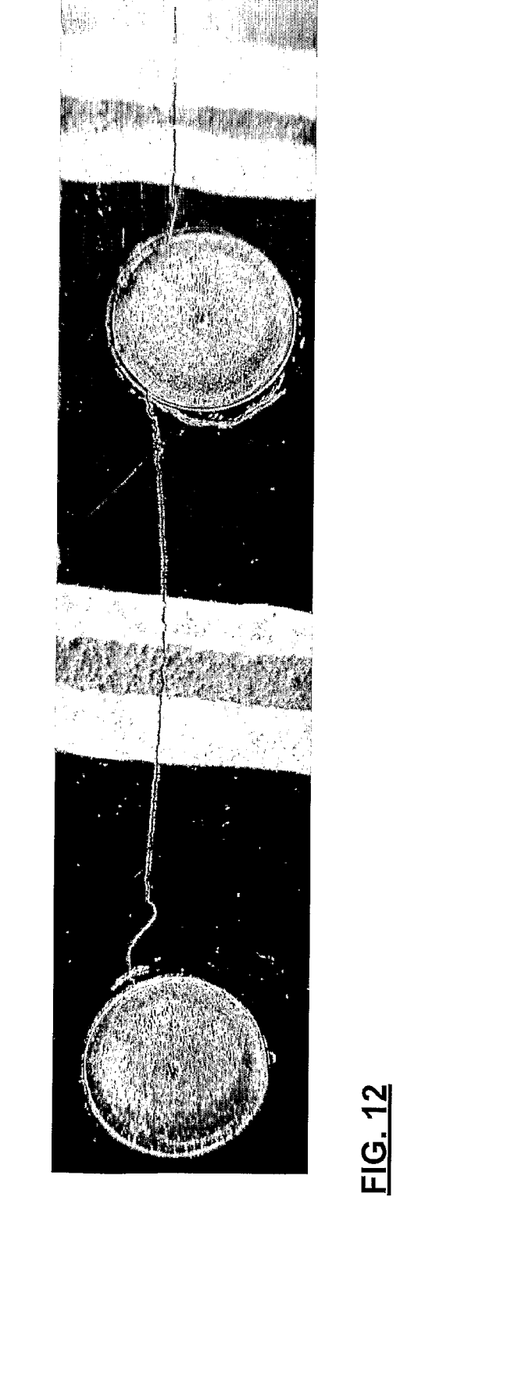
FIG. 12 is an image of a crack passing through the surface-mounted crack sensor of FIG. 7.

FIG. 12 is an enlarged image of a crack formed through the aluminum test coupon.

It will be appreciated that the surface-mounted sensor according to the invention can be customized to any complex shape and bridge across built-up constructs composed of a mix of differing materials.

What is claimed is:

1. A crack detector on a surface of an article, the crack detector comprising:
   a brittle undercoat composed of a cementitious compound principally formed of a fine particulate composition with a binding agent adhered to the surface; and
   a trace of electrically conductive ink or paint adhered to the undercoat, such that the trace is separated from the surface by the undercoat, said trace including at least one region adapted to allow an electronic interrogator to determine electrical continuity of the trace.

2. The crack detector according to claim 1 wherein the trace provides at least two terminals for connection to the electronic interrogator, and the electronic interrogator determines one of a current and a voltage across the trace.

3. The crack detector according to claim 1 wherein the trace consists of a plurality of traces arrayed to provide an indication of a size or position of a crack.

4. The crack detector according to claim 1 wherein the trace is of a shape defining an antenna, and the electronic interrogator energizes the antenna with electromagnetic energy, whereby a failure of the antenna to absorb the electromagnetic energy indicates a break in the trace.

5. The crack detector according to claim 1 wherein:
   the trace includes a terminal for electrical connection with the electronic interrogator;
   the trace defines a capacitor with a conductive surface separated from the trace by a thin insulating layer; and
   the interrogator determines a capacitance of the capacitor.

6. The crack detector according to claim 4 wherein the conductive surface is the structural surface, which is electrically conductive, and the thin insulating layer is the undercoat.

7. The crack detector according to claim 4 wherein the conductive surface is a second trace of the electrically conductive ink or paint applied on top of a second coat of the cementitious compound that overlays the trace.

8. The crack detector according to claim 4 wherein the conductive surface is a second trace on the undercoat and wherein the trace and second trace include a plurality of segments such that segments of the trace are paired with segments of the second trace, and the paired traces are parallel.

9. The crack detector according to claim 1 wherein the fine particulate composition consists essentially of alumina, magnesia, silica, or zirconia ceramics.

10. The crack detector according to claim 1 wherein the cementitious compound consists of a thermocouple cement.

11. The crack detector according to claim 1 wherein the surface is a structural surface of the article.

12. The crack detector according to claim 11 further comprising a protective coat of the cementitious compound that covers the trace but permits electrical continuity determination by the electronic interrogator.

13. The crack detector according to claim 11 further comprising an electronic interrogator embedded on the structural surface in electrical connection with the trace.

14. The crack detector according to claim 13 wherein the electronic interrogator provide a wireless communications function.

15. The crack detector according to claim 14 wherein the electronic interrogator comprises a radio frequency identification tag.

16. A method of monitoring a surface for deformation, said method comprising:
   a) applying a cementitious compound principally formed of a fine particulate composition with a binding agent to the surface to produce a brittle undercoat;
   b) applying an electrically conductive trace on the undercoat; and
   c) assessing electrical continuity of the trace.

17. The method according to claim 16 wherein applying the undercoat comprises painting the undercoat onto the surface using a brush, a roll, or a spray.

18. The method according to claim 17 wherein painting the undercoat comprises painting the undercoat onto the surface through a template.

19. The method according to claim 16 wherein applying the electrically conductive trace to the undercoat comprises drawing the trace with one of a conductive ink pen and an ink jet, painting the trace with a roller, spray or brush through a template, or transferring a pattern of ink on to the surface through one of a stamp, and a pad printer.

20. The method according to claim 16 wherein assessing electrical conductivity along the trace comprises connecting probes of a voltage detector to two points on the trace, energizing the trace, which defines an antenna, with electromagnetic energy, or determining a capacitance through the brittle undercoat responsive to a voltage difference between the trace and the surface, which is electrically conductive.

21. The method according to claim 16 further comprising applying a protective coating over the trace leaving only at least two terminals of the trace exposed.

22. A kit for producing a surface-mounted crack sensor, the kit comprising:
   a) a cementitious compound principally formed of a fine particulate composition with a binding agent; and
   b) an electrically conductive ink or paint.

23. A kit according to claim 21 further comprising one or more of:
   c) instructions for:
      applying the cementitious compound to a surface to form a brittle undercoat; and
      applying the electrically conductive ink or paint to define a trace on the undercoat;
   d) an RFID tag for electrical connection to the trace, the RFID tag being adapted to interrogate a surface-mounted crack sensor produced with the kit;
   e) a thin film conductive surface for deposition over the trace to capacitively couple the trace with the conductive surface; and
   f) a pattern-form for producing the trace.

* * * * *